(12) United States Patent
Maeda (10) Patent No.: US 9,606,033 B2
(45) Date of Patent: Mar. 28, 2017

(54) AUTOSAMPLER

(71) Applicant: SHIMADZU CORPORATION, Kyoto-shi, Kyoto (JP)

(72) Inventor: Yoshiaki Maeda, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/017,824

(22) Filed: Feb. 8, 2016

(65) Prior Publication Data

US 2016/0274011 A1 Sep. 22, 2016

(30) Foreign Application Priority Data

Mar. 19, 2015 (JP) ................. 2015-055820

(51) Int. Cl.
| | |
|---|---|
| *G01N 1/42* | (2006.01) |
| *G01N 1/10* | (2006.01) |
| *G01N 35/10* | (2006.01) |
| *G01N 30/24* | (2006.01) |
| *G01N 35/00* | (2006.01) |
| *G01N 35/04* | (2006.01) |

(52) U.S. Cl.
CPC ............. *G01N 1/42* (2013.01); *G01N 30/24* (2013.01); *G01N 35/1011* (2013.01); *G01N 2035/00346* (2013.01); *G01N 2035/00356* (2013.01); *G01N 2035/0491* (2013.01)

(58) Field of Classification Search
CPC .................................. G01N 1/42; G01N 1/10
USPC .......................................................... 73/863.11
See application file for complete search history.

(56) References Cited

U.S. PATENT DOCUMENTS

| | | | | |
|---|---|---|---|---|
| 5,212,097 A | * | 5/1993 | Kamahori | G01N 33/58 436/111 |
| 5,277,871 A | * | 1/1994 | Fujii | G01N 30/88 210/656 |
| 5,408,307 A | * | 4/1995 | Yamamoto | G01N 15/1456 356/336 |
| 5,783,450 A | * | 7/1998 | Yoshida | G01N 30/88 422/70 |
| 2012/0222502 A1 | * | 9/2012 | Nakano | G01N 30/24 73/864.91 |
| 2015/0143929 A1 | * | 5/2015 | Volckens | G01N 1/2202 73/863.11 |

* cited by examiner

*Primary Examiner* — Lisa Caputo
*Assistant Examiner* — Jamel Williams
(74) *Attorney, Agent, or Firm* — Westerman, Hattori, Daniels & Adrian, LLP (57) ABSTRACT

According to an embodiment of an autosampler, a sample rack provided with a thermal conductive plate holder on whose upper surface a sample plate is to be set is set on a rack setting section. A cooling device for cooling the plate holder is provided. A plate detection section for detecting whether a sample plate is set on the plate holder of the sample rack that is set on the rack setting section is provided, and when a sample plate is not set on the plate holder of the sample rack that is set on the rack setting section, the output of the cooling device for cooling the plate holder is turned off.

6 Claims, 6 Drawing Sheets

AUTOSAMPLER

BACKGROUND OF THE INVENTION

1. Field of the Invention

The present invention relates to an autosampler for automatically collecting a sample at a liquid chromatograph, and for introducing the sample into an analytical path that is communicated with an analytical column.

2. Description of the Related Art

An autosampler for a high performance liquid chromatograph (HPLC) or an autosampler for an ultra high performance liquid chromatograph (UHPLC) may be provided with a function for controlling the temperature of an analysis target sample that is placed inside the device to a predetermined temperature (see US 2012/0222502 A1). According to such an autosampler, a microplate containing a sample or a plate on which a sample container is set (hereinafter such plate(s) will be referred to as sample plate(s)) is set on a sample rack, and the sample rack is set inside a sample accommodation chamber of the autosampler.

The part of the sample rack where the sample plate is to be set is formed from a material with high thermal conductivity, and a cooling device for cooling the sample rack is provided inside the sample accommodation chamber of the autosampler. The temperature of an analysis target sample on the sample plate that is set on the sample rack is controlled to, for example, 10° C. or less by cooling the sample rack accommodated in the sample accommodation chamber by the cooling device.

SUMMARY OF THE INVENTION

According to an autosampler as described above, a space may be provided to one sample rack for setting two or more sample plates. With such an autosampler, when a sample rack with a vacant setting space for a sample plate is set inside the sample accommodation chamber, the surface of the vacant setting space of the sample rack stays exposed inside the sample accommodation chamber and is cooled by the cooling device to a temperature lower than the temperature inside the chamber, for example, 5° C. Dew is generated at the portion of the vacant setting space, causing problems such as leakage of the dew to outside the chamber when the sample rack is drawn out from the sample accommodation chamber and breakage of a mechanism inside the autosampler.

Accordingly, the present invention aims to prevent generation of dew on the surface of a sample rack that is set inside a sample accommodation chamber of an autosampler.

A mode of an autosampler according to the present invention includes a sample rack provided with a thermal conductive plate holder on whose upper surface a sample plate is to be set, a rack setting section on which the sample rack is to be set, a cooling device for cooling the plate holder of the sample rack that is set on the rack setting section, a plate detection section for detecting whether a sample plate is set on the plate holder of the sample rack that is set on the rack setting section, and a cooling control section for turning off an output of the cooling device for cooling the plate holder of the sample rack that is set on the rack setting section when, according to a detection result for a sample plate by the plate detection section, a sample plate is not set on the plate holder.

A mode of an autosampler according to the present invention includes the plate detection section for detecting whether a sample plate is set on the plate holder of the sample rack, and if a sample plate is not set on the plate holder of the sample rack that is set on the rack setting section, the output of the cooling device for cooling the plate holder is turned off, and thus the plate holder on which a sample plate is not set is prevented from being cooled, and generation of dew on the surface of the plate holder is prevented.

DETAILED DESCRIPTION OF THE INVENTION

As an embodiment of an autosampler according to the present invention, one with a sample rack which is provided with a plurality of plate holders may be cited. In such a case, desirably, the plate holders are thermally separated from one another, a cooling device is provided to the rack setting section so as to individually cool each plate holder of the sample rack, and a cooling control section is configured to turn off, based on a detection result for a sample plate by a plate detection section, the output of the cooling device for the plate holder on which a sample plate is not set, among the plate holders of the sample rack set on a rack setting section. This allows the plate holders among the plate holders provided in the sample rack on which sample plates are set to be cooled while allowing plate holder on which sample plates are not set to be not cooled and preventing generation of dew.

In order to output a signal according to presence/absence of a sample plate on each plate holder of the sample rack set at the rack setting section, the plate detection section according to a preferred embodiment of the autosampler according to the present invention may be configured from a plurality of plate sensors provided at positions corresponding to respective plate holders on the rack setting section, and a plate presence determination section for determining presence or absence of a sample plate on each plate holder based on an output signal from the plate sensor.

Also, in a more preferred embodiment of the autosampler according to the present invention, there may further be provided a needle assembly which includes a needle whose tip end faces vertically downward in order to collect a sample in a sample plate set on a plate holder of the sample rack set on the rack setting section, and which moves the needle in a horizontal plane direction and a vertical direction at above the rack setting section, the needle assembly including a needle-side sensor for outputting a signal according to presence/absence of a sample plate at a time of lowering of the needle at a predetermined position above the rack setting section. In this case, the plate detection section is preferably comprised of the needle-side sensor, and a plate presence determination section for determining presence or absence of a sample plate on each plate holder based on the output signal from the needle-side sensor. This allows detection of presence or absence of a sample plate on the sample rack without separately providing a sensor for detecting the sample plate, and the cost may be reduced.

An example of the autosampler will be described with reference to FIGS. 1 and 2.

Two rack tables 2a and 2b are provided, as rack setting sections, inside a sample accommodation chamber of the autosampler. A sample rack 16 is set on the upper surface of each of the rack tables 2a and 2b. A plate holder 18, which is an setting space for setting a sample plate 22, is provided at two positions of the sample rack 16 set on each of the rack tables 2a and 2b. The sample plate 22 is, for example, a microplate provided with a plurality of sample reservoirs or a plate for setting a plurality of sample vials.

Additionally, in the present example, two rack tables 2a and 2b are provided as the rack setting sections, but the number of rack setting sections may be one or three or more. Also, in the present example, two plate holders 18 are provided to the sample rack 16, but three or more plate holders may alternatively be provided.

The part of the sample rack 16 other than the plate holders 18 is formed from a heat insulation material such as resin, such as polypropylene (PP) or polybutylene terephthalate (PBT), and a foam-based heat insulation material, for example, and only the plate holders 18 are formed from a thermal conductive material such as iron, copper, aluminum or the like. The plate holders 18 are provided being spaced apart, and are thermally separated from each other. The surfaces of the plate holders 18 are exposed to the surface of the sample rack 16, and the back surfaces of the plate holders 18 are exposed to the back surface of the sample rack 16.

Although not shown, a recessed section for fitting a protrusion provided to the back surface of the sample plate 22 is provided to the plate holder 18, for example, and the sample plate 22 is positioned on the plate holder 18 by the protrusion of the sample plate 22 being fitted into the recessed section.

The sample rack 16 is set on each of the rack tables 2a and 2b by being slid on the rack table 2a or 2b from one end side of the rack table 2a or 2b (the right side in the drawing) until the tip end portion of the sample rack 16 (the left end portion in the drawing) contacts a stopper 11 provided at the other end side of the rack table 2a or 2b (the left side in the drawing).

Rack sensors 6a and 6b are provided, correspondingly to the rack tables 2a and 2b, on an inner wall surface 10 at the deepest section of the sample accommodation chamber. The rack sensors 6a and 6b are U-shaped microsensors having a light emitting section and a light receiving section arranged facing each other. A sector 20 further protruding from the tip end side of the sample rack 16 is provided to the tip end portion of the sample rack 16. The sector 20 is inserted between the light emitting section and the light receiving section of the rack sensor 6a or 6b when the sample rack 16 is slid on the rack table 2a or 2b until it contacts the stopper 11. When the sector 20 is inserted between the light emitting section and the light receiving section of the rack sensor 6a or 6b, the rack sensor 6a or 6b is switched from an on state to an off state, and setting of the sample rack 16 on the rack table 2a or 2b is detected.

The rack table 2a includes thermal conductive sections 5a-1 and 5a-2 at two positions that are in contact with the lower surfaces of the plate holders 18 of the sample rack 16 set on the rack table 2a. The rack table 2a other than the thermal conductive sections 5a-1 and 5a-2 is formed from a heat insulation material such as a foam-based heat insulation material, and the thermal conductive sections 5a-1 and 5a-2 are thermally separated from each other.

Cooling devices 4a-1 and 4a-2 which are formed, for example, by Peltier devices and which are independently driven are provided on the underside of the thermal conductive sections 5a-1 and 5a-2, respectively, and the plate holders 18 that are in contact with the thermal conductive sections 5a-1 and 5a-2 are cooled by the cooling devices 4a-1 and 4a-2, and the temperature of the sample plates 22 set on the plate holders 18 is thus cooled to a predetermined temperature. The thermal conductive sections 5a-1 and 5a-2 are, for example, heat absorption surfaces of the cooling devices 4a-1 and 4a-2 exposed at the upper surface of the rack table 2a.

Temperature sensors 9a-1 and 9a-2 are embedded in the thermal conductive sections 5a-1 and 5a-2, respectively. The outputs of the cooling devices 4a-1 and 4a-2 are controlled based on output signals of the temperature sensors 9a-1 and 9a-2 in such a way that the temperature of the thermal conductive sections 5a-1 and 5a-2 is at a temperature that is set in advance.

Plate sensors 8a-1 and 8a-2, each for detecting presence or absence of the sample plate 22 on the plate holder 18 of the sample rack 16 set on the rack table 2a, are provided. In the present example, the plate sensors 8a-1 and 8a-2 are provided at positions, at a side of the rack table 2a, corresponding to the thermal conductive sections 5a-1 and 5a-2. As the plate sensors 8a-1 and 8a-2, micro switches, photo sensors, reflection sensors, or the like may be used.

The rack table 2b and its peripheral structures are structured in the same way as the rack table 2a and its peripheral structures, and thus, description of the rack table 2b and its peripheral structures is omitted.

A needle assembly 12 including a needle 14 for collecting a sample from the sample plate 22 is provided above the rack tables 2a and 2b. The needle assembly 12 is for moving the needle 14 in a horizontal plane direction and a vertical direction.

Figure 3:
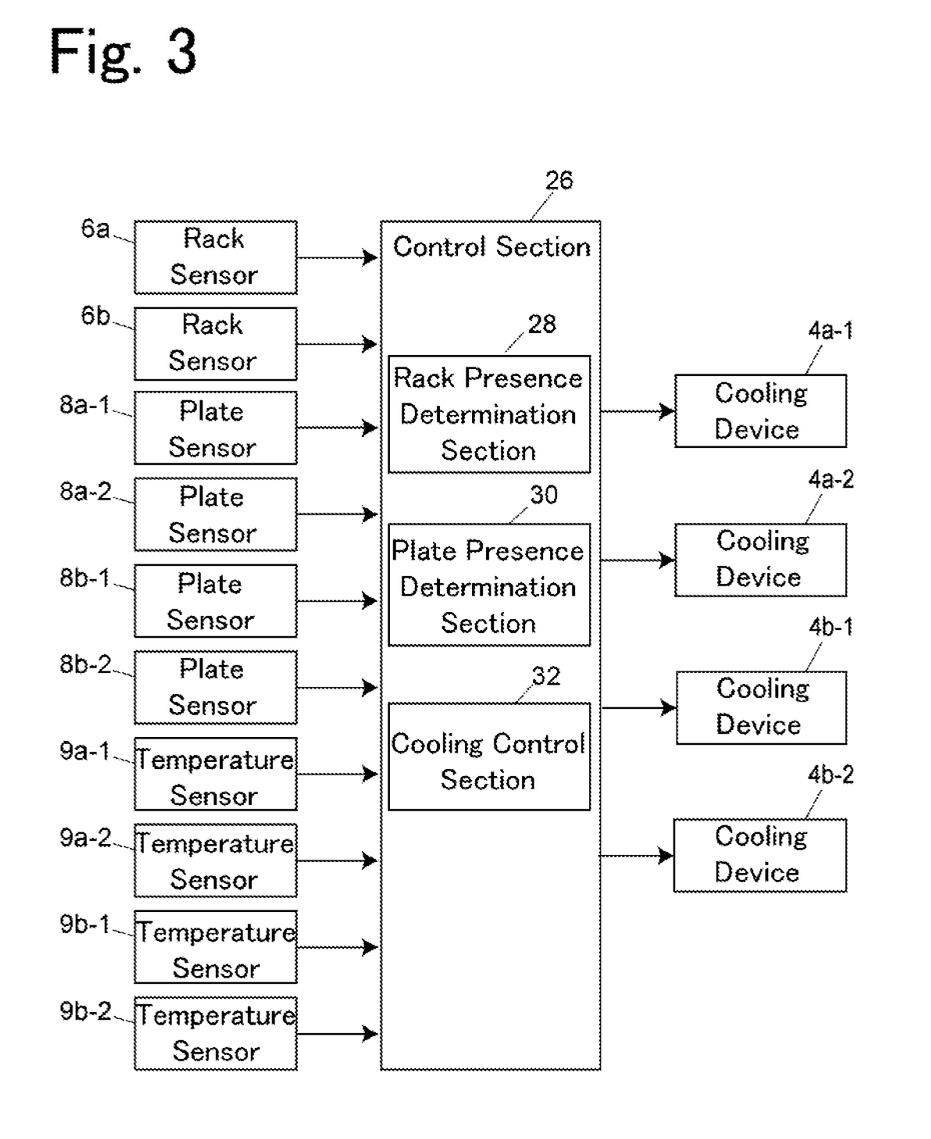
FIG. 3 is a block diagram showing an example of a control system of the present example.

Next, a control system of the present example will be described with reference to FIG. 3.

Outputs of the cooling devices 4a-1, 4a-2, 4b-1, and 4b-2 are controlled by a control section 26. Output signals of the rack sensors 6a and 6b, the plate sensors 8a-1, 8a-2, 8b-1, and 8b-2, and the temperature sensors 9a-1, 9a-2, 9b-1, and 9b-2 are captured by the control section 26. The control section 26 individually controls the outputs of the cooling devices 4a-1, 4a-2, 4b-1, and 4b-2 based on these signals. The control section 26 is comprised of a storage device storing predetermined programs, and an arithmetic device comprised of a computer that executes the programs stored in the storage device.

The control section 26 includes a rack presence determination section 28, a plate presence determination section 30, and a cooling control section 32. The rack presence determination section 28, the plate presence determination section 30, and the cooling control section 32 are functions that can be achieved by the programs stored in the storage device configuring the control section 26 and by the arithmetic device executing the programs.

The rack presence determination section 28 determines, based on output signals from the rack sensors 6a and 6b, whether the sample rack 16 is set on the rack tables 2a and 2b.

The plate presence determination section 30 determines, based on output signals from the plate sensors 8a-1, 8a-2, 8b-1, and 8b-2, whether the sample plate 22 is set on the thermal conductive sections 5a-1, 5a-2, 5b-1, and 5b-2. The plate sensors 8a-1, 8a-2, 8b-1, and 8b-2, and the plate presence determination section 30 comprise the plate detection section for detecting presence or absence of the sample plate 22 on each of the thermal conductive sections 5a-1, 5a-2, 5b-1, and 5b-2.

The cooling control section 32 individually controls outputs of the cooling devices 4a-1, 4a-2, 4b-1, and 4b-2 based on output signals from the temperature sensors 9a-1, 9a-2, 9b-1, and 9b-2 so that the temperature of each of the thermal conductive sections 5a-1, 5a-2, 5b-1, and 5b-2 will be at a temperature set in advance.

Furthermore, the cooling control section 32 switches the output of each of the cooling devices 4a-1, 4a-2, 4b-1, and 4b-2 between on and off based on the determination results of the rack presence determination section 28 and the plate presence determination section 30. That is, in the case where the sample rack 16 is set on only one or none of the rack tables 2a and 2b, the output of the cooling device provided to the rack table 2a or 2b on which the sample rack 16 is not set is turned off. Moreover, in the case where, although the sample rack 16 is set, the sample rack 16 includes a plate holder 18 on which the sample plate 22 is not set, the output of the cooling device for the plate holder 18 is turned off. For example, in FIG. 2, the sample plate 22 is not set on the plate holder 18 on the base end side (the right side in the drawing) of the sample rack 16 set on the rack table 2b, and thus, the output of the cooling device 4b-2 is turned off.

Figure 4:
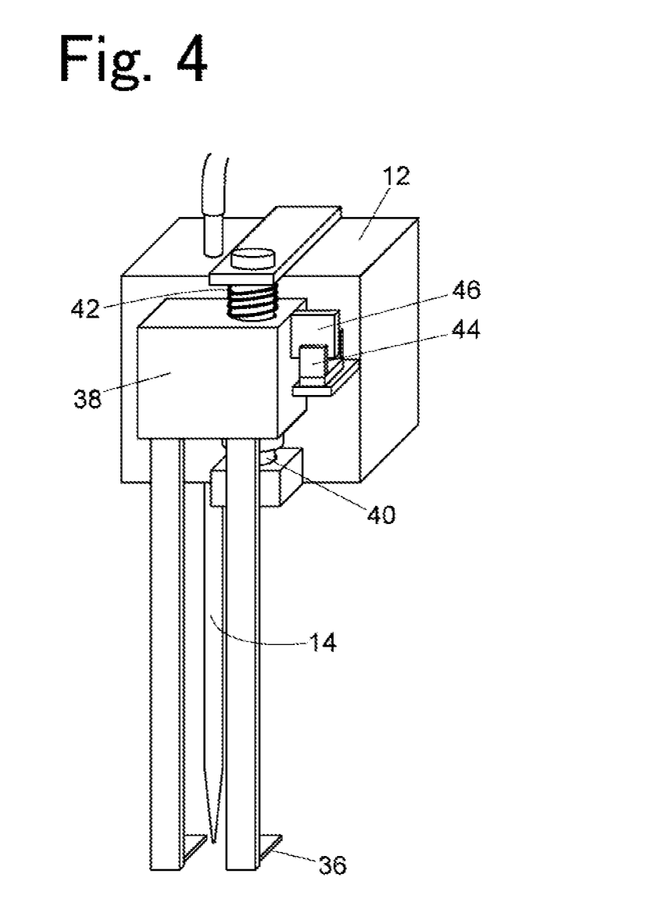
FIG. 4 is a perspective view showing an example of a needle assembly of the present example.

An example of the needle assembly 12 is shown in FIG. 4.

The needle assembly 12 of this example includes a container holder 36 extending downward from the main body of the needle assembly 12 to beyond the tip end of the needle 14. The container holder 36 prevents, at the time of the needle assembly 12 moving downward from above a sample container so as to insert the tip end of the needle 14 into the sample container, the sample container from being toppled over by the lower end portion contacting the sample container before the tip end of the needle 14. The base end of the container holder 36 is held by a block 38 that is capable of moving, in the vertical direction with respect to the needle assembly 12, along a shaft 40 that is fixed to the main body of the needle assembly 12 in the vertical direction. The block 38 is biased downward at all times by a compressed elastic body such as a coil spring.

A U-shaped micro switch 44 (needle-side sensor) is provided to the main body of the needle assembly 12, and a sector 46 for switching the micro switch 44 between on and off is provided to the block 38. Normally, that is, when the lower end of the container holder 36 is not in contact with a sample container or the like, the sector 46 is inserted between a light emitting section and a light receiving section of the micro switch 44, and the micro switch 44 is in an off state. When the needle assembly 12 moves further downward in a state where the lower end of the container holder 36 is in contact with a sample container or the like, the positional relationship between the block 38 and the main body of the needle assembly 12 is changed, and the sector 46 is thereby detached from the micro switch 44 and the micro switch 44 is turned on. Presence or absence of a sample container is determined based on whether the micro switch 44 is turned on or not when the needle assembly 12 is lowered to a specific height.

As described above, in the case where the micro switch 44 is provided to the needle assembly 12, the micro switch 44 may be used, instead of the plate sensors 8a-1, 8a-2, 8b-1, and 8b-2, as the sensor for detecting presence or absence of the sample plate 22 on each of the thermal conductive sections 5a-1, 5a-2, 5b-1, and 5b-2.

Figure 5:
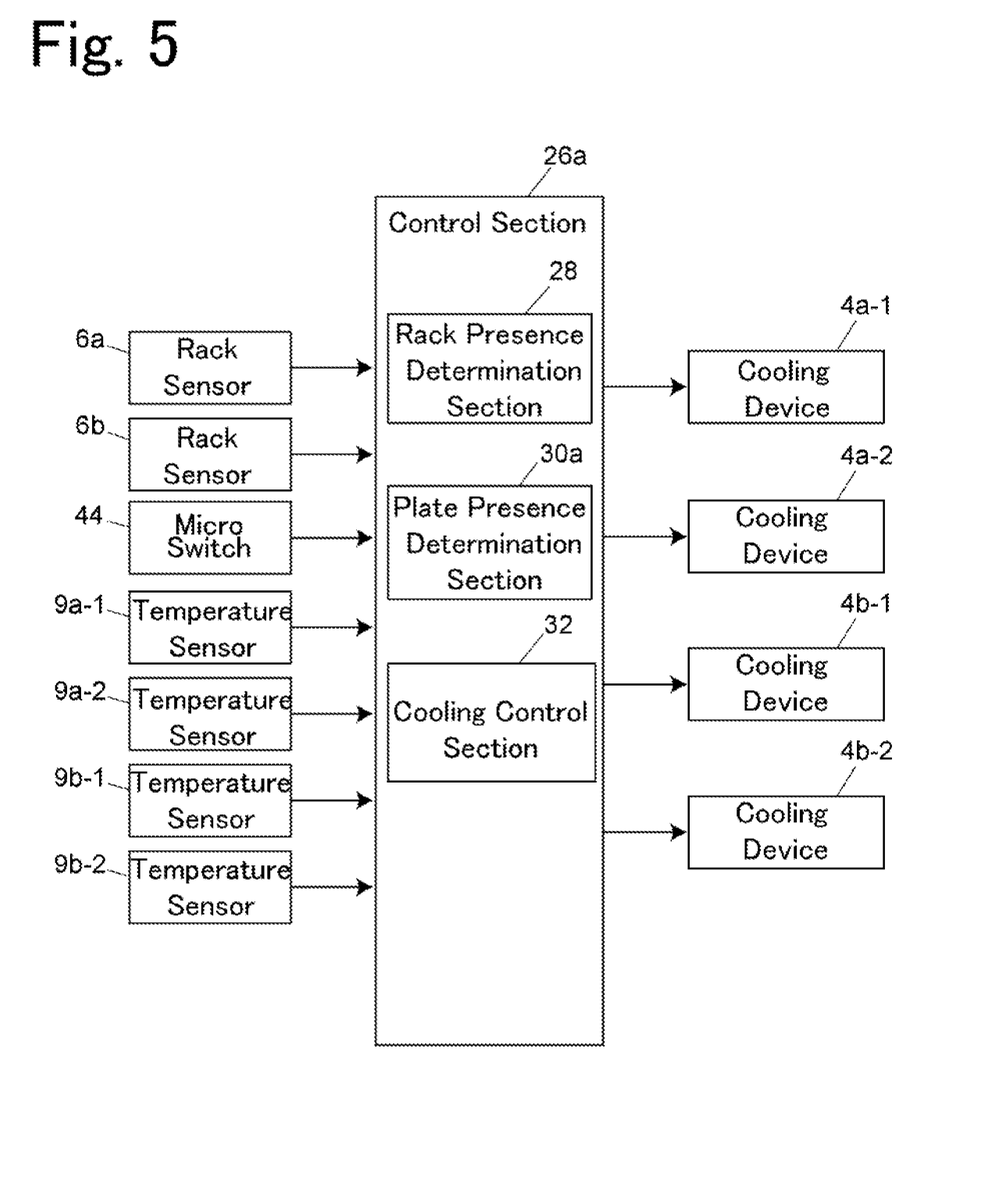
FIG. 5 is a block diagram showing a control system of another example of the autosampler.

As shown in FIG. 5, in the case of using the micro switch 44 as the sensor for detecting presence or absence of the sample plate 22, an output signal of the micro switch 44 is captured by a control section 26a. The control section 26a is provided with a plate presence determination section 30a for determining presence or absence of the sample plate 22 on each of the thermal conductive sections 5a-1, 5a-2, 5b-1, and 5b-2 based on the output signal from the micro switch 44. The micro switch 44 and the plate presence determination section 30a comprise the plate detection section for detecting presence or absence of the sample plate 22 on each of the thermal conductive sections 5a-1, 5a-2, 5b-1, and 5b-2.

If, when the needle assembly 12 is lowered from above a predetermined position of each of the thermal conductive sections 5a-1, 5a-2, 5b-1, and 5b-2, the sample plate 22 is present at the position, the micro switch 44 is turned on by the lower end of the container holder 36 coming into contact with the sample plate 22 or a sample container set on the sample plate 22. The plate presence determination section 30a is comprised to determine whether the sample plate 22 is present at each position on the thermal conductive sections 5a-1, 5a-2, 5b-1, and 5b-2 based on whether the micro switch 44 is turned on when the needle assembly 12 is lowered by a specific distance from above a predetermined position of each of the thermal conductive sections 5a-1, 5a-2, 5b-1, and 5b-2 at a timing when presence or absence of the sample plate 22 is to be detected.

Figure 6:
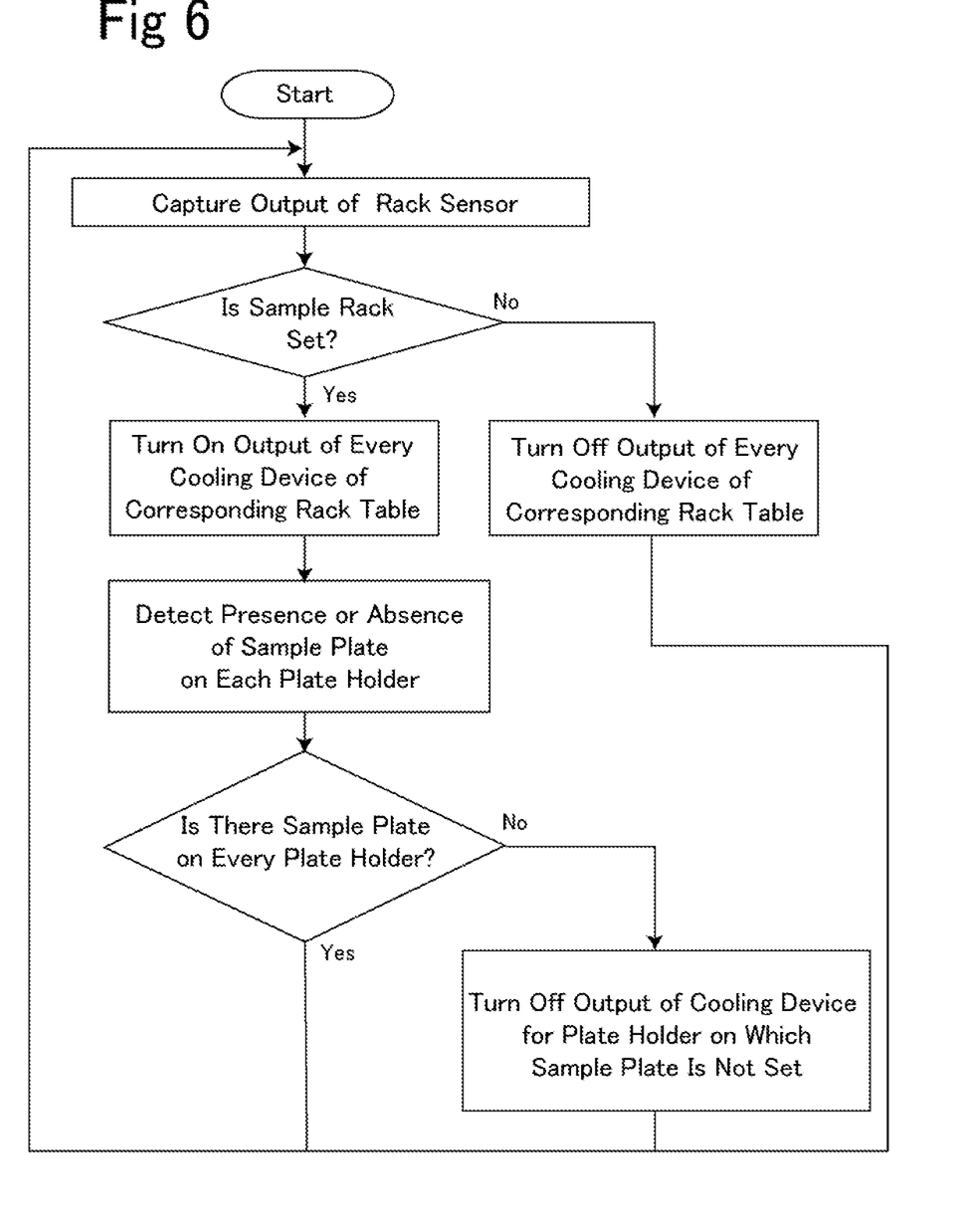
FIG. 6 is a flow chart showing an example of an output management operation of a cooling device of the present example.

Next, an output management operation for each of the cooling devices 4a-1, 4a-2, 4b-1, and 4b-2 by the control section 26 will be described with reference to FIGS. 1, 2, and 3, and the flow chart in FIG. 6. Additionally, with the autosampler of the present example, driving of the cooling devices 4a-1, 4a-2, 4b-1, and 4b-2 started when power is turned on, and then the following output management operation is started.

In the present example, the following operation is performed alternately or simultaneously at the rack table 2a side and the rack table 2b side. Here, description will be given on the rack table 2a, but the same thing can be said for the rack table 2b.

First, an output signal from the rack sensor 6a is captured, and whether the sample rack 16 is set on the rack table 2a is detected. In the case where the sample rack 16 is set, the outputs of the cooling devices 4a-1 and 4a-2 provided to the rack table 2a are turned on, and temperature control based on the temperature sensors 5a-1 and 5a-2 is started. In the case where the sample rack 16 is not set, the outputs of the cooling devices 4a-1 and 4a-2 provided to the rack table 2a are turned off.

If the sample rack 16 is set on the rack table 2a, and the outputs of the cooling devices 4a-1 and 4a-2 are turned on, presence or absence of the sample plate 22 on each of the plate holders 18 (each of the thermal conductive sections 5a-1 and 5a-2) of the sample rack 16 is detected. As in the example described with reference to FIGS. 1 to 3, in the case where the plate sensors 8a-1 and 8a-2 for detecting presence or absence of the sample plate 22 on respective thermal conductive sections 5a-1 and 5a-2 are provided, the presence or absence of the sample plate 22 is detected based on the output signals from the plate sensors 8a-1 and 8a-2. On the other hand, in the case of detecting the presence or absence of the sample plate 22 on each of the thermal conductive sections 5a-1 and 5a-2 based on the output signal from the needle-side sensor (micro switch 44) shown in FIG. 4, the presence or absence of the sample plate 22 is detected by lowering the needle assembly 12 by a specific distance from a predetermined position of each of the thermal conductive sections 5a-1 and 5a-2 and by using the output signal from the micro switch 44 at this time.

If there is the sample plate 22 on every plate holder 18, the outputs of the cooling devices 4a-1 and 4a-2 are maintained in the on state, and if the sample plate 22 is not present on a plate holder 18, that is, if there is a vacant plate holder 18, the output of the cooling device 4a-1 or 4a-2 corresponding to the vacant plate holder 18 is turned off.

By sequentially performing the operation described above, the thermal conductive sections 5a-1 and 5a-2 and the plate holders 18 that are exposed inside the sample accommodation chamber of the autosampler are prevented from being cooled, and generation of dew on the surfaces thereof is prevented.

Additionally, in the example described above, a case is described where a plurality of plate holders 18 are provided to one sample rack 16, and the cooling devices 4a-1, 4a-2, 4b-1, and 4b-2 of the number corresponding to the plate holders 18 are provided, but the present invention also includes a case where one sample rack is cooled by one cooling device regardless of the number of plate holders.

Figure 1:
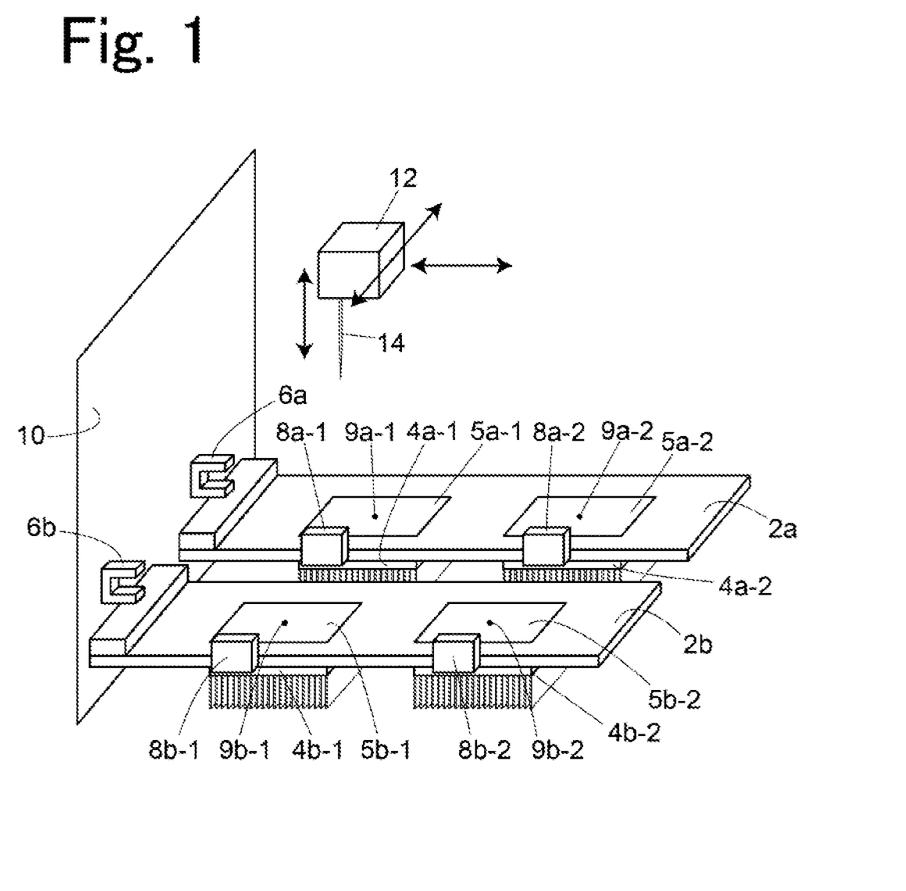
FIG. 1 is a perspective view schematically showing a configuration of the inside a sample accommodation chamber of an example of an autosampler.
Figure 2:
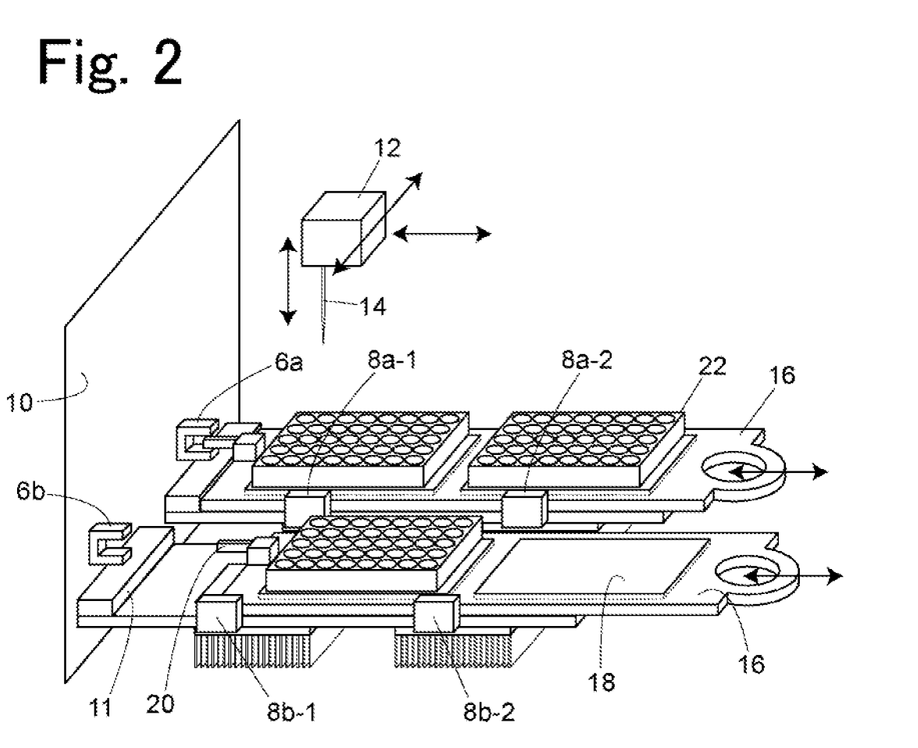
FIG. 2 is a perspective view showing the inside of the sample accommodation chamber of the present example together with a sample rack.

Referring to FIG. 1, for example, a case is described where one cooling device is provided for each of the rack tables 2a and 2b. In such a case, when the sample rack 16 is set on the rack table 2a or 2b, if the sample plate 22 is not set on the plate holder 18 of the sample rack 16, the output of the cooling device for cooling the sample rack 16 is turned off, and generation of dew is prevented. As shown in FIG. 2, when the sample plate 22 is not set on one of the plate holders 18 of the sample racks 16, the output of the cooling device of the rack table 2a or 2b on which the sample rack 16 is set (2b in FIG. 2) is turned off.

Also, a function for allowing a user to select either cooling of the sample plate 22 or prevention of generation of dew as the priority may be provided as another function of the device, and in the case where cooling of the sample plate 22 is prioritized, the output of the cooling device may be turned on if the sample plate 22 is set on at least one of the plate holders 18 of the sample racks 16, and in the case where prevention of generation of dew is prioritized, the output of the cooling device may be turned off if there is even one plate holder 18, of the sample racks 16, on which the sample plate 22 is not set.

What is claimed is:

1. An autosampler comprising:
    a sample rack provided with a thermal conductive plate holder on whose upper surface a sample plate is to be set:
    a rack setting section on which the sample rack is to be set;
    a cooling device for cooling the plate holder of the sample rack set on the rack setting section;
    a plate detection section for detecting whether a sample plate is set on the plate holder of the sample rack set on the rack setting section; and
    a cooling control section for turning off an output of the cooling device for cooling the plate holder of the sample rack set on the rack setting section when, according to a detection result for a sample plate by the plate detection section, a sample plate is not set on the plate holder.

2. The autosampler according to claim 1,
    wherein the sample rack includes a plurality of the plate holders, and the plate holders are thermally separated from each other,
    wherein the cooling device is provided to the rack setting section so as to individually cool the plate holder of the sample rack, and
    wherein the cooling control section is configured to turn off the output of the cooling device for the plate holder on which a sample plate is not set, among the plate holders of the sample rack set on the rack setting section, based on detection results for a sample plate by the plate detection section.

3. The autosampler according to claim 2, wherein, in order to output a signal according to presence/absence of a sample plate on the plate holder of the sample rack set on the rack setting section, the plate detection section is comprised of plate sensors provided at positions corresponding to the plate holders on the rack setting section, and a plate presence determination section for determining presence or absence of a sample plate on the plate holders based on output signals from the plate sensors.

4. The autosampler according to claim 2, further comprising
    a needle assembly that includes a needle whose tip end faces vertically downward in order to collect a sample in a sample plate set on the plate holder of the sample rack that is set on the rack setting section, and that moves the needle in a horizontal plane direction and a vertical direction at above the rack setting section, the needle assembly including a needle-side sensor for outputting a signal according to presence/absence of the sample plate at a time of lowering of the needle at a predetermined position above the rack setting section,
    wherein the plate detection section is comprised of the needle-side sensor, and a plate presence determination section for determining presence or absence of a sample plate on each plate holder based on an output signal from the needle-side sensor.

5. The autosampler according to claim 1, wherein, in order to output a signal according to presence/absence of a sample plate on the plate holder of the sample rack that is set on the rack setting section, the plate detection section is comprised of plate sensors that are provided at positions corresponding to the plate holders on the rack setting section, and a plate presence determination section for determining presence or absence of a sample plate on the plate holders based on output signals from the plate sensors.

6. The autosampler according to claim 1, further comprising
    a needle assembly that includes a needle whose tip end faces vertically downward in order to collect a sample in a sample plate set on the plate holder of the sample rack that is set on the rack setting section, and that moves the needle in a horizontal plane direction and a vertical direction at above the rack setting section, the needle assembly including a needle-side sensor for outputting a signal according to presence absence of the sample plate at a time of lowering of the needle at a predetermined position above the rack setting section,
    wherein the plate detection section is comprised of the needle-side sensor, and a plate presence determination section for determining presence or absence of a sample plate on each plate holder based on an output signal from the needle-side sensor.

* * * * *